United States Patent [19]

Botrè et al.

[11] Patent Number: 4,940,793
[45] Date of Patent: Jul. 10, 1990

[54] PHARMACOLOGICALLY ACTIVE PIPERAZINO DERIVATIVES

[75] Inventors: Francesco Botrè, Rome; Roberto Signorini, Milan, both of Italy

[73] Assignee: Ravizza S.p.a., Milan, Italy

[21] Appl. No.: 756,257

[22] Filed: Jul. 18, 1985

[30] Foreign Application Priority Data

Aug. 14, 1984 [IT] Italy ................... 22334 A/84

[51] Int. Cl.$^5$ ............... C07D 487/04; C07D 295/10; C07D 295/22
[52] U.S. Cl. ..................... 544/349; 544/367; 544/368; 544/370; 544/372; 544/377; 544/382; 544/383; 544/386; 544/390; 544/391; 544/392
[58] Field of Search ............ 544/349, 366, 367, 372, 544/377, 386, 368, 370, 382, 383, 388, 390, 392, 391

[56] References Cited

U.S. PATENT DOCUMENTS

| | | | |
|---|---|---|---|
| 3,865,828 | 2/1975 | Korosi et al. | 544/365 |
| 4,374,990 | 2/1983 | Weber et al. | 544/363 |
| 4,386,098 | 5/1983 | Woltersdorf, Jr. et al. | 514/367 |

FOREIGN PATENT DOCUMENTS 2414498 10/1975 Fed. Rep. of Germany.

OTHER PUBLICATIONS

"Pharmazeutische Chemie", E. Schroder et al, 1982, p. 754, Georg Thieme Verlag Stuttgart, New York (partial translation attached).
"Arzneimittel Wirkungen", E. Mutschler, 1981, p. 484, Wissenschaftliche Verlagsgessellschaft mbH Stuttgart (partial translation attached).
Carter et al, Biology and Chemistry of the Carbonic Anhydrases, vol. 429, Jun. 29, 1984, Contents.
Botre et al, Journal of Medicinal Chemistry, 1986, 29,1814.
Liebenow et al., Chem. Abst. 90-103673j.
Liebenow et al., Chem. Abst. 84-4696p.
Buyer, Medicinal Chemistry, 2nd Edition, 1960, pp. 800-803.
In re Weber, 198 USPO 328.

*Primary Examiner*—Cecilia Shen
*Attorney, Agent, or Firm*—Stevens, Davis, Miller & Mosher

[57] ABSTRACT

New piperazino derivatives of formula

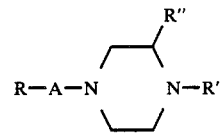

in which R is a phenyl radical substituted with at least one sulphonamido group or a substituted nitrogenated heterocyclic ring, and A is CO, $CH_2$, $SO_2$, possessing inhibiting activity towards carbonic anhydrase.

The new products are prepared from compounds of formula R-A-X in which X is OH, SH, halogen, OR'''' or SR'''' in which R'''' is methyl, ethyl, phenyl, carbomethoxy, carboethoxy, and from a piperazino derivative of formula

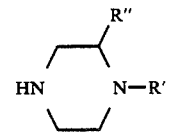

The R' group can also be introduced on termination of the reaction, by removing and substituting a protective group present at the nitrogen.

1 Claim, No Drawings

PHARMACOLOGICALLY ACTIVE PIPERAZINO DERIVATIVES

This invention relates to a new class of pharmacologically active piperazino derivatives, and the process for their preparation.

More precisely, the invention relates to a new class of piperazino derivatives possessing inhibiting activity towards carbonic anhydrase. Carbonic anhydrase is known to be one of the most widespread enzymes in human tissues, and plays a determining role in many physiological and pathological processes.

Consequently its inhibition can be a factor in the solution of therapeutical problems of considerable importance.

The new compounds according to the present invention are those of general formula:

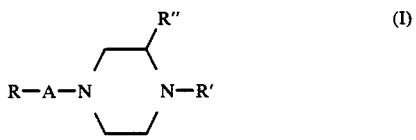

in which R is a phenyl radical containing at least one sulphonamido group and possibly various substituents chosen from the group consisting of halogen, $C_1$–$C_4$ alkyl, $C_1$–$C_4$ alkoxy; or a nitrogenated heterocyclic ring containing as substituent at least one amino, amido or sulphonamido group;

A is CO, $CH_2$, $SO_2$;

R' is H, alkyl, alkenyl, alkyl-aryl, alkyl-cycloalkyl, alkyl-acyl, alkyl-carboxyalkoxy, alkyl-carboxyamino, alkenyl-aryl, alkenylcycloalkyl, alkenyl-acyl, alkenyl-carboxyalkoxy, alkenyl-carboxyamino, acyl, aryl;

R" is H or together with R' and with the nitrogen atom to which this latter is bonded forms a heterocyclic ring, provided that when R is a substituted phenyl radical and A is CO, R' is other than H, $C_1$–$C_4$ alkyl, benzyl.

Preferred meanings of the indicated radicals are as follows:

R is 2-methoxy-5-sulphamoyl-phenyl, 2-sulphamoyl-imidazyl, 2-amino or 2-acetamido-1,3,4-thiadiazole;

R' is H, linear or branched $C_1$–$C_6$ alkyl, linear or branched $C_1$–$C_6$ alkenyl, alkyl-phenyl or alkenyl-phenyl in which the phenyl group is either simple or substituted with halogens, trihalomethyls, $C_1$–$C_6$ alkyls, $C_1$–$C_6$ alkoxys, $C_1$–$C_6$ alkylethers, sulphonamido groups; $C_2$–$C_6$ aliphatic acyl; alkyl-acyl radical in which the acyl is $C_1$–$C_6$ aliphatic, aromatic or nitrogenated heterocyclic; $C_3$–$C_6$ alkyl-carboxyalkoxy; alkyl-carboxyamino in which the alkyl is $C_1$–$C_3$ and the amine is mono or disubstituted with linear or branched $C_1$–$C_6$ alkyl radicals;

R" is H or together with R' forms a 5 or 6 term ring condensed with the piperazine, but again taking into account said limitation that when R is a substituted phenyl radical and A is CO, R' is other than H, $C_1$–$C_4$ alkyl, benzyl.

The new products according to the present invention are prepared essentially in accordance with the following reaction:

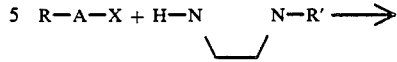

where R, R', R" are as heretofore defined,

X is OH, SH, Cl, Br, I, OR'''', SR'''' in which R'''' is methyl, ethyl, phenyl, carbomethoxy, carboethoxy, in the presence of a base or a condensing agent.

The R' substituents can be introduced to the piperazino nitrogen either before or after reaction (II) is effected, using known methods comprising reacting the piperazino nitrogen bonded to the hydrogen with the required compound containing a reactive group.

Preferably, when the R' substituents are introduced to the piperazino ring as the final stage of the process, reaction (II) is effected beforehand using benzyl-piperazine

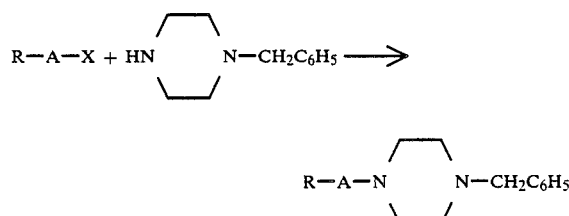

The benzyl derivative thus obtained is debenzylsted by catalytic hydrogenation with Pd on C, and the compound obtained

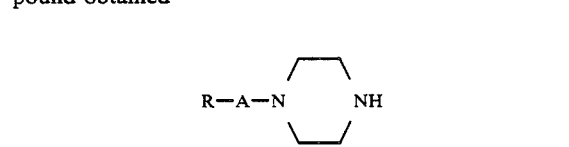

is reacted with a suitable compound YR', in which Y is a reactive group, preferably halogen.

It is in any case apparent that instead of the benzyl group, use can be made of any other suitable protective group of one of the piperazino nitrogens, which can be eliminated when reaction (II) is terminated.

The R'-R" cyclisation can also be effected before or after effecting reaction (II).

Reaction (II) is preferably effected by reacting, with the compound R-A-OH and $PCl_3$ or $POCl_5$ in a basic medium, the piperazino derivative containing the group R' or with one of the nitrogens suitably protected.

The amine:R-A-OH:$PCl_3$ ratio is generally stoichiometric, or has a slight deficiency (10–20%) of the compound R-A-OH relative to the stoichiometric.

The basic medium is preferably pyridine, or any organic basic solvent able to block the HCl which forms during the reaction. The reaction takes place under hot conditions, preferably at the mixture reflux temperature.

The product obtained is separated and purified by normal methods.

In particular, it is purified by repeated crystalliastions either as such or in the form of the hydrochloride. The compounds in which A is CH$_2$ can be prepared by reducing the corresponding compounds in which A is CO, obtained by process (II).

Some practical examples are described hereinafter in order to better clarify the process according to the present invention and make it more easily reproducible, but these are to be considered as purely illustrative and in no case limitative of the process according to the present invention.

EXAMPLE 1

Preparation of the compound of formula

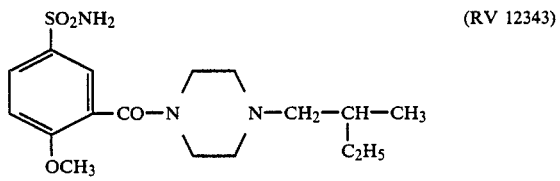
(RV 12343)

A solution of N(2-methyl-1-butyl)piperazine in pyridine with an aminetpyridine weight ratio of 1:10 was fed into a suitable reactor, and a cold solution of PCl$_3$ in pyridine in a weight ratio of 1:10 was dripped in. The mixture was kept under agitation for one hour at ambient temperature, after which 2-methoxy-5-sulphamoyl-benzoic acid was added, and the mixture heated under reflux for 4 hours.

Amine:PCl$_3$:acid molar ratio=3:1:2.5

The cooled reaction mixture was evaporated under vacuum, taken up in dilute 10% sodium hydroxide solution, washed with ether, acidified with acetic acid and filtered over carbon.

The clear solution was alkalised with concentrated ammonia under agitation.

The precipitate was filtered off after some hours and washed with water.

The product RV 12343 in the form of the hydrochloride was purified by repeated crystallisations from n.butanol. Yield 65% with respect to the acid.

M.P.=184°-186° C. n.c.

| Percentage anslysis: C$_{17}$H$_{27}$N$_3$O$_4$S.HCl; MW 405.93 | | | |
|---|---|---|---|
| calculated | C 50.30 | H 6.95 | N 10.35 |
| found | 50.24 | 7.11 | 10.25 |

EXAMPLE 2

Preparation of the compound of formula

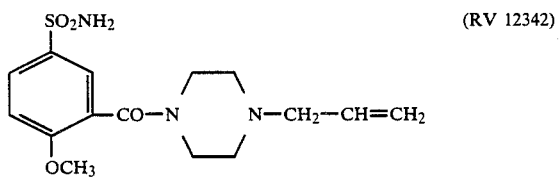
(RV 12342)

A solution of N-allyl-piperazine in pyridine with an amine:solvent weight ratio of 1:15 was fed into the reactor, and a cold solution of PCl$_3$ in pyridine in a weight ratio of 1:10 was dripped in. The mixture was kept under agitation for one hour at ambient temperature, after which 2-methoxy-5-sulphamoyl-benzoic acid was added, and the mixture heated under reflux for 4 hours.

Amine:PCl$_3$ acid molar ratio=3:1:3

The cooled reaction mixture was evaporated to dryness under vacuum, taken up in dilute 20% sodium hydroxide solution, washed with chloroform, acidified with acetic acid and filtered over carbon.

The clear solution was alkalised with 1N NaOH and left for some hours under agitation.

The precipitate was then filtered off, washed with water and recrystallised from ethyl acetate. Yield 35%.

The pure product had the following characteristics:

M.P.=104°-105° C. n.c.

| Percentage analysis: C$_{15}$H$_{21}$N$_3$O$_4$S; MW 339.41 | | | |
|---|---|---|---|
| calculated | C 53.08 | H 6.23 | N 12.38 |
| found | 53.09 | 6.30 | 12.10 |

EXAMPLE 3

Preparation of the compound of formula

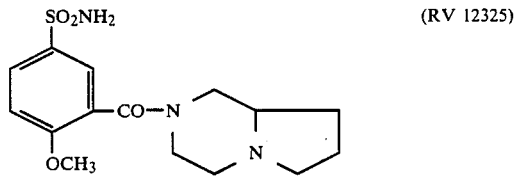
(RV 12325)

A solution of diazobicyclononane in pyridine with an amine:solvent weight ratio of 1:10 was fed into the reactor, and a cold solution of PCl$_3$ in pyridine in a weight ratio of 1:10 was dripped in.

The mixture was kept under agitation for one hour at ambient temperature, after which 2-methoxy-5-sulphamoyl-benzoic acid was added, and the mixture heated under reflux for 4 hours. Amine:PCl$_3$:acid ratio=3:1:3.

The reaction mixture was evaporated to dryness under vacuum, taken up in dilute sodium hydroxide solution, washed with ether, acidified with acetic acid and filtered over carbon.

The clear solution was alkalised with concentrated NH$_4$OH under agitation. The product does not precipitate, and it is therefore extracted with chloroform, washed with water, the organic phase evaporated to dryness, and crystallised from isopropyl alcohol. Yield 68%.

M.P.=123°-125° C.

| Percentage analysis: C$_{15}$H$_{21}$N$_3$O$_4$S; MW 339.42 | | | |
|---|---|---|---|
| calculated | C 53.08 | H 6.24 | N 12.38 |
| found | 53.30 | 6.50 | 12.10 |

EXAMPLE 4

Preparation of the compound of formula

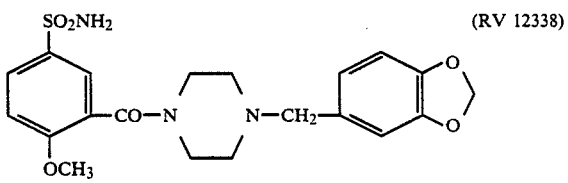
(RV 12338)

A solution of piperonylpiperazine in pyridine with an amine:solvent weight ratio of 1:12 was fed into the reactor, and a cold solution of PCl₃ in pyridine in a weight ratio of 1:10 was dripped in.

The mixture was kept under agitation for one hour at ambient temperature, after which 2-methoxy-5-sulphamoyl-benzoic acid was added and the mixture heated under reflux for 4 hours. Amine:PCl₃:acid ratio=3:1:2.7

The reaction mixture was evaporated to dryness under vacuum, taken up in dilute sodium hydroxide solution, washed with CCl₄, acidified with dilute hydrochloric acid and filtered over carbon. The clear solution was alkalised with concentrated NH₄OH under agitation.

The precipitate was filtered off, washed with water and recrystallised from ethyl alcohol. Yield 40%.
M.P.=185°–186° C.

| Percentage analysis: $C_{20}H_{23}N_3O_6S$; MW 433.48 | | | |
|---|---|---|---|
| calculated | C 55.42 | H 5.35 | N 9.69 |
| found | 55.37 | 5.55 | 9.59 |

EXAMPLE 5

Preparation of the compound of formula

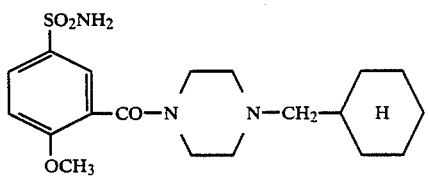
(RV 12344)

A solution of 1-cyclohexyl-methyl-piperazine in pyridine with an amine:solvent weight ratio of 1:10 was fed into the reactor, and a cold solution of PCl₃ in pyridine in a weight ratio of 1:10 was dripped in.

The mixture was kept under agitation for one hour at ambient temperature, after which 2-methoxy-5-sulphamoyl-benzoic acid was added and the mixture heated under reflux for 4 hours. Amine:PCl₃ acid ratio=3:1:2.5

The reaction mixture was evaporated to dryness under vacuum, taken up in dilute sodium hydroxide solution, washed with ether, acidified with acetic acid and filtered over carbon.

The clear solution was alkalised with concentrated Na₂CO₃ under agitation. The slightly tacky precipitate was filtered off, washed with water. dissolved in acidified water and reprecipitated with dilute ammonia. Yield 40%.
M.P.=110°–112° C.

| Percentage analsyis: $C_{19}H_{29}N_3O_4S$; MW 395.52 | | | |
|---|---|---|---|
| calculated | C 57.70 | H 7.39 | N 10.62 |
| found | 57.55 | 7.37 | 10.39 |

EXAMPLE 6

Preparation of the compound of formula

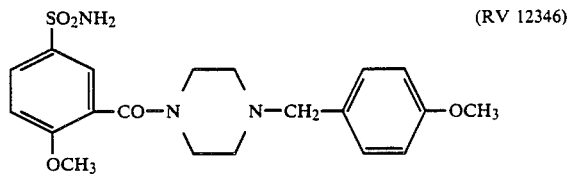
(RV 12346)

A solution of 4-methoxy-benzylpiperszine in pyridine with an amine: solvent weight ratio of 1:15 was fed into the reactor, and a cold solution of PCl₃ in pyridine in a weight ratio of 1:10 was dripped in.

The mixture was kept under agitation for 2 hours at ambient temperature, after which 2-methoxy-5-sulphamoyl-benzoic acid was added and the mixture heated under reflux for 3 hours. Amine:PCl₃:acid ratio=3:1:3

The reaction mixture was evaporated to dryness under vacuum, taken up in dilute sodium hydroxide solution, washed with chloroform, acidified with acetic acid and filtered over carbon. The clear solution was alkalised with concentrated NH₄OH under agitation. The precipitate was filtered off and washed with water. The acid base treatment was repeated and the solid obtained was crystallised from isopropanol. Yield 65%.
M.P.=160°–162° C.

| Percentage analysis: $C_{20}H_{25}N_3O_5S$; MW 419.49 | | | |
|---|---|---|---|
| calculated | C 57.26 | H 6.00 | N 10.02 |
| found | 57.34 | 6.15 | 9.91 |

EXAMPLE 7

Preparation of the compound of formula

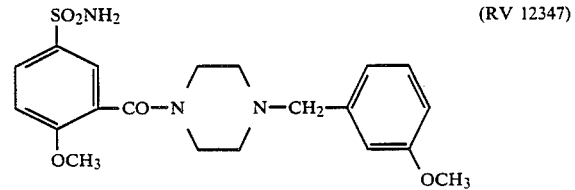
(RV 12347)

A solution of 3-methoxy-benzyl-piperazine in pyridine with an amine:solvent weight ratio of 1:10 was fed into the reactor, and a cold solution of PCl₃ in pyridine in a weight ratio of 1:10 was dripped in.

The mixture was kept under agitation for 1.5 hours at ambient temperature, after which 2-methoxy-5-sulphamoyl-benzoic acid was added and the mixture heated under reflux for 4 hours. Amine:PCl₃:acid ratio=3:1:3

The reaction mixture was evaporated to dryness under vacuum, taken up in dilute sodium hydroxide solution, washed with CH₂Cl₂, acidified with acetic acid and filtered over carbon.

The clear solution was alkalised with 1N KOH under agitation. The precipitate was filtered off, washed with water and recrystallised from isopropyl alcohol. Yield 67%.

M.P. = 178°–179° C.

| Percentage analysis: C20H25N3O5S; MW 419.49 | | | |
|---|---|---|---|
| calculated | C 57.26 | H 6.00 | N 10.02 |
| found | 57.43 | 6.09 | 10.20 |

EXAMPLE 8

Preparation of the compound of formula

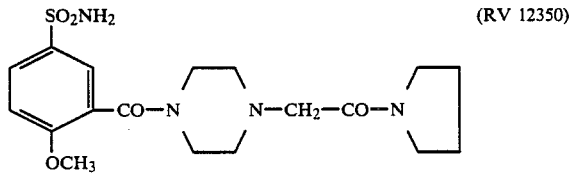
(RV 12350)

A solution of pyrrolidino-carbonyl-N-methyl-piperazine in pyridine with an amine:solvent weight ratio of 1:10 was fed into the reactor, and a cold solution of PCl3 in pyridine in a weight ratio of 1:10 was dripped in.

The mixture was kept under agitation for one hour at ambient temperature, after which 2-methoxy-5-sulphamoyl-benzoic acid was added and the mixture heated under reflux for 5 hours. Amine:PCl3:acid ratio = 3:1:3.5

The reaction mixture was evaporated to dryness under vacuum, taken up in dilute sodium hydroxide solution, washed with ether, acidified with acetic acid and filtered over carbon. The clear solution was alkalised with concentrated NH4OH under agitation. The tacky precipitate was extracted with ethyl acetate, washed with water and evaporated to dryness. The residue was taken up in slightly alkaline water and solidified under agitation. It was filtered off and crystallised from aqueous ethyl alcohol. Yield 60%. M.P. = 205°–206° C.

| Percentage analysis: C18H26N4O5S.½H2O; MW 419.50 | | | |
|---|---|---|---|
| calculated | C 51.83 | H 6.49 | N 13.30 |
| found | 51.70 | 6.38 | 13.15 |

EXAMPLE 9

Preparation of the compound of formula

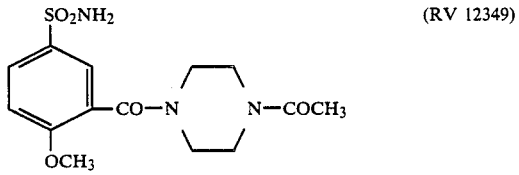
(RV 12349)

Benzyl-piperazine, PCl3 and 2-methoxy-5-sulphamoyl-benzoic acid were reacted in a reactor in accordance with the method described in Example 1. The product of formula

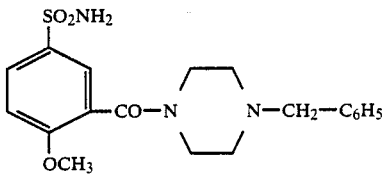

was separated, and debenzylated by catalytic reduction with 5% Pd on C in ethyl alcohol.

The 2-methoxy-5-sulphamoyl-benzoylpiperazine obtained in this manner was reacted with acetyl chloride in a molar ratio of 1:1, in benzene in the presence of pyridine, was filtered off, washed and crystallised from a mixture of methanol and ethyl acetate. Yield 70%.

M.P. = 208°–210° C.

| Percentage analysis: C14H19N3O5S.½H2O; MW 350.38 | | | |
|---|---|---|---|
| calculated | C 47.96 | H 5.71 | N 11.90 |
| found | 48.17 | 5.72 | 11.76 |

EXAMPLE 10

Preparation of the compound of formula

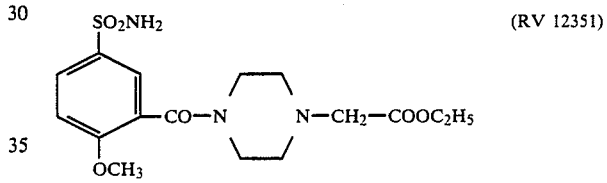
(RV 12351)

A solution of ethoxycarbonyl-methyl-piperazine in pyridine with an amine:solvent weight ratio of 1:10 was fed into the reactor, and a cold solution of PCl3 in pyridine in a weight ratio of 1:10 was dripped in.

The mixture was kept under agitation for one hour at ambient temperature, after which 2-methoxy-5-sulphamoyl-benzoic acid was added and the mixture heated under reflux for 3 hours. Amine:PCl3:acid ratio = 3:1:3.

The reaction mixture was evaporated to dryness under vacuum, taken up in dilute sodium hydroxide solution, washed with ether, acidified with acetic acid and filtered over carbon.

The clear solution was alkalised with concentrated NH4OH under agitation. The tacky precipitate was extracted with ethyl acetate, precipitated with alcoholic HCl, filtered off and crystallised from ethanol. Yield 40%.

M.P. = 225° C. (hydrochloride)

| Percentage analysis: C16H23N3O6S.Hcl; MW 421.90 | | | |
|---|---|---|---|
| calculated | C 45.55 | H 5.73 | N 9.95 |
| found | 45.39 | 5.63 | 9.77 |

EXAMPLE 11

Preparation of the compound of formula

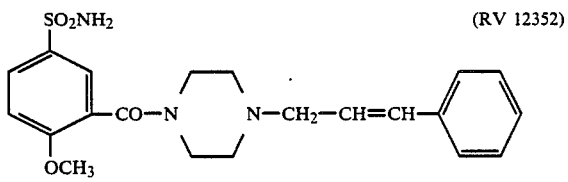
(RV 12352)

A solution of cinnamyl-piperazine in pyridine with an amine:solvent weight ratio of 1:12 was fed into the reactor, and a cold solution of PCl₃ in pyridine in a weight ratio of 1:10 was dripped in.

The mixture was kept under agitation for 2 hours at ambient temperature, after which 2-methoxy-5-sulphamoyl-benzoic acid was added and the mixture heated under reflux for 4 hours. Amine:PCl₃:acid ratio=3:1:2.5

The reaction mixture was evaporated to dryness under vacuum, taken up in dilute sodium hydroxide solution, washed with ether, acidified with acetic acid and filtered over carbon.

The clear solution was alkalised with concentrated NaOH under agitation. The precipitate was filtered off, washed with water and recrystallised from isopropyl alcohol. Yield 60%. M.P.=110° C.

| Percentage analysis: $C_{21}H_{25}N_3O_4S \cdot \frac{1}{2}H_2O$; MW 424.5 | | | |
|---|---|---|---|
| calculated | C 59.42 | H 6.17 | N 9.89 |
| found | 59.33 | 6.24 | 9.81 |

EXAMPLE 12

Preparation of the compound of formula

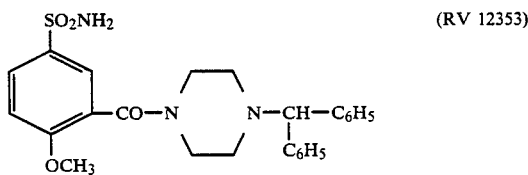
(RV 12353)

A solution of benzhydryl-piperazine in pyridine with an amine:solvent weight ratio of 1:10 was fed into the reactor, and a cold solution of PCl₃ in pyridine in a weight ratio of 1:10 was dripped in.

The mixture was kept under agitation for one hour at ambient temperature, after which 2-methoxy-5-sulphamoyl-benzoic acid was added and the mixture heated under reflux for 4 hours. Amine:PCl₃:acid ratio=3:1:3.

The reaction mixture was evaporated to dryness under vacuum, taken up in dilute sodium hydroxide solution, washed with CCl₄, acidified with acetic acid and filtered over carbon.

The clear solution was alkalised with concentrated NH₄OH under agitation. The precipitate was filtered off, washed with water and recrystallised from ethanol. Yield 61%.
M.P.=255°–257° C.

| Percentage analysis: $C_{25}H_{27}N_3O_4S$; MW 465.58 | | | |
|---|---|---|---|
| calculated | C 64.49 | H 5.84 | 9.02 |
| found | 64.29 | 5.91 | 8.89 |

EXAMPLE 13

Preparation of the compound of formula

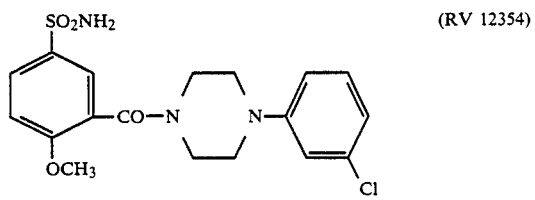
(RV 12354)

A solution of N(3Cl-phenyl)piperazine in pyridine with an amine:solvent weight ratio of 1:10 was fed into the reactor, and a cold solution of PCl₃ in pyridine in a weight ratio of 1:10 was dripped in.

The mixture was kept under agitation for 2 hours at ambient temperature, after which 2-methoxy-5-sulphamoyl-benzoic acid was added and the mixture heated under reflux for 2 hours. Amine:PCl₃:acid ratio=3:1:2.7

The reaction mixture was evaporated to dryness under vacuum, taken up in dilute sodium hydroxide solution, washed with ether, acidified with acetic acid and filtered over carbon.

The clear solution was alkalised with concentrated NH₄OH under agitation. The precipitate was filtered off and washed with water. The acid-base treatment was repeated, and the solid obtained was crystallised from aqueous methanol. Yield 60%.
M.P.=105°–107° C.

| Percentage analysis: $C_{18}H_{20}ClN_3O_4S \cdot \frac{1}{2}H_2O$; MW 418.89 | | | | | |
|---|---|---|---|---|---|
| calculated | C | 51.61 | H | 5.05 | N 10.03 |
| found | | 51.48 | | 4.92 | 9.95 |

EXAMPLE 14

Preparation of the compound of formula

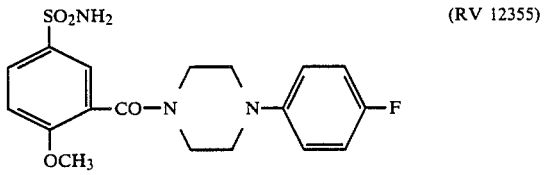
(RV 12355)

A solution of N(4fluoro-phenyl)-piperazine in pyridine with an amine:solvent weight ratio of 1:12 was fed into the reactor, and a cold solution of PCl₃ in pyridine in a weight ratio of 1:10 was dripped in.

The mixture was kept under agitation for one hour at ambient temperature, after which 2-methoxy-5-sulphamoyl-benzoic acid was added and the mixture heated under reflux for 3 hours. Amine:PCl₃:acid ratio=3:1:3

The reaction mixture was evaporated to dryness under vacuum, taken up in dilute sodium hydroxide solution, washed with ether, acidified with acetic acid and filtered over carbon.

The clear solution was alkalised with concentrated NH₄OH under agitation. The precipitate was filtered off, washed with water and recrystallised from ethanol. Yield 30%.
M.P.=195°–197° C.

| Percentage analysis: $C_{18}H_{20}FN_3O_4S$; MW 393.44 | | | | | | |
|---|---|---|---|---|---|---|
| calculated | C | 54.95 | H | 5.12 | N | 10.68 |
| found | | 54.89 | | 5.15 | | 10.59 |

EXAMPLE 15

Preparation of the compound of formula

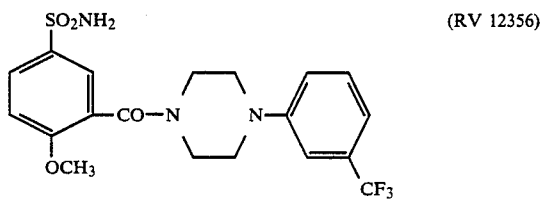

(RV 12356)

A solution of N(3-trifluoromethyl-phenyl)piperazine in pyridine with an amine:solvent weight ratio of 1:10 was fed into the reactor, and a solution of $PCl_3$ in pyridine in a weight ratio of 1:10 was dripped in.

The mixture was kept under agitation for 1.5 hours at ambient temperature, after which 2-methoxy-5-sulphamoyl-benzoic acid was added and the mixture heated under reflux for 4 hours. Amine:$PCl_3$:acid ratio = 3:1:2.5

The reaction mixture was evaporated to dryness under vacuum, taken up in dilute sodium hydroxide solution, washed with $CHCl_3$, acidified with acetic acid and filtered over carbon.

The clear solution was alkalised with concentrated NaOH under agitation. The precipitate was filtered off, washed with water and recrystallised from ethanol. Yield 32%.

M.P. = 125°–127° C.

| Percentage analysis: $C_{19}H_{20}F_3N_3O_4S \cdot \frac{1}{2}H_2O$; MW 452.45 | | | | | | |
|---|---|---|---|---|---|---|
| calculated | C | 50.43 | H | 4.68 | N | 9.27 |
| found | | 50.60 | | 4.75 | | 9.13 |

EXAMPLE 16

Preparation of the compound of formula

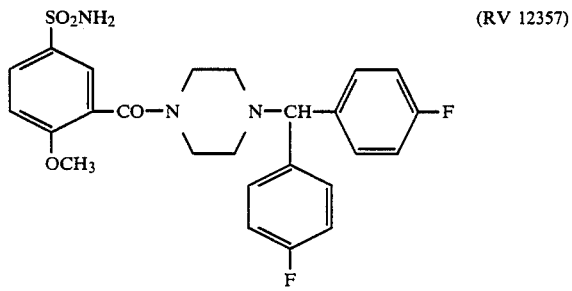

(RV 12357)

A solution of bis(4F-phenyl)-methyl-piperazine in pyridine with an amine:solvent weight ratio of 1:10 was fed into the reactor, and a cold solution of $PCl_3$ in pyridine in a weight ratio of 1:10 was dripped in.

The mixture was kept under agitation for 2 hours at ambient temperature, after which 2-methoxy-5-sulphamoyl-benzoic acid was added, and the mixture heated under reflux for 4 hours. Amine:$PCl_3$:acid ratio = 3:1:3

The reaction mixture was evaporated to dryness under vacuum, taken up in dilute sodium hydroxide solution, washed with ether, acidified with acetic acid and filtered over carbon.

The clear solution was alkalised with concentrated $NH_4OH$ under agitation. The precipitate was filtered off, washed with water and recrystallised from n.butanol. Yield 56%.

M.P. = 238°–240° C.

| Percentage analysis: $C_{25}H_{25}F_2N_3O_4S$; MW 501.56 | | | | | | |
|---|---|---|---|---|---|---|
| calculated | C | 59.86 | H | 5.02 | N | 8.37 |
| found | | 59.68 | | 5.10 | | 8.22 |

EXAMPLE 17

Preparation of the compound of formula

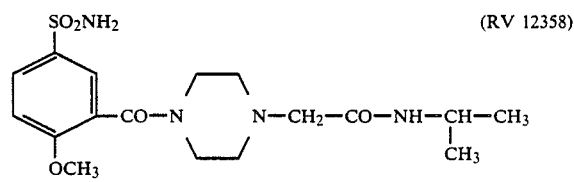

(RV 12358)

A solution of isopropyl-amino-carbonyl-methyl-piperazine in pyridine with an amine:solvent weight ratio of 1:10 was fed into the reactor, and a cold solution of $PCl_3$ in pyridine in a weight ratio of 1:10 was dripped in.

The mixture was kept under agitation for one hour at ambient temperature, after which 2-methoxy-5-sulphamoyl-benzoic acid was added and the mixture heated under reflux for 2 hours. Amine:$PCl_3$:acid ratio = 3:1:2.5

The reaction mixture was evaporated to dryness under vacuum, taken up in dilute sodium hydroxide solution, washed with ether, acidified with acetic acid and filtered over carbon.

The clear solution was alkalised with concentrated $NH_4OH$ under agitation. The precipitate was filtered off, washed with water and recrystallised from ethanol. Yield 48%.

M.P. = 228°–230° C.

| Percentage analysis: $C_{17}H_{26}N_4O_5S$; MW 398.48 | | | | | | |
|---|---|---|---|---|---|---|
| calculated | C | 51.24 | H | 6.57 | N | 14.06 |
| found | | 50.99 | | 6.61 | | 13.94 |

EXAMPLE 18

Preparation of the compound of formula

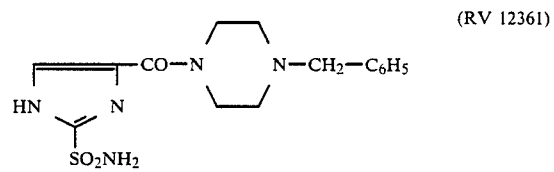

(RV 12361)

A solution of benzyl-piperazine in pyridine with an amine:solvent weight ratio of 1:15 was fed into the reactor, and a cold solution of $PCl_3$ in pyridine in a weight ratio of 1:10 was dripped in.

The mixture was kept under agitation for one hour at ambient temperature, after which 2-sulphamoyl-4-imidazole carboxylic acid was added and the mixture heated under reflux for 3 hours. Amine:PCl$_3$:acid ratio=3:1:3.

The reaction mixture was evaporated to dryness under vacuum, taken up in dilute sodium hydroxide solution, washed with ether, acidified with acetic acid and filtered over carbon.

The clear solution was alkalised with concentrated NH$_4$OH under agitation. The precipitate was filtered off, washed off, washed with water and recrystallised from n.butanol. Yield 30%.

M.P.=224°–225° C.

| Percentage analysis: C$_{15}$H$_{19}$N$_5$O$_3$S; MW 349.40 | | | | | | |
|---|---|---|---|---|---|---|
| calculated | C | 51.56 | H | 5.48 | N | 20.04 |
| found | | 51.39 | | 5.41 | | 19.87 |

EXAMPLE 19

Preparation of the compound of formula

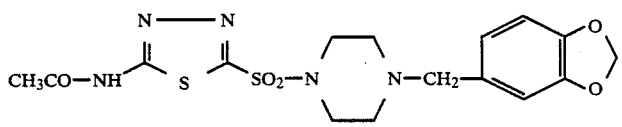

2-acetamido-1,3,4-thiadiazole 5-sulphochloride and piperonylpiperazine in stoichiometric ratio were fed in CHCl$_3$ solution into the reactor.

The mixture was kept under agitation for 4–5 hours, cooling it with ice, after which it was evaporated to dryness under vacuum and the residue was taken up in dilute sodium hydroxide solution, washed with ether, acidified with acetic acid and filtered over carbon.

The clear solution was alkalised with concentrated NH$_4$OH under agitation. The precipitate was filtered off, washed with water and recrystallised from ethanol. Yield 70%.

M.P.=238°–240° C.

| Percentage analysis: C$_{16}$H$_{19}$N$_5$O$_5$S$_2$.½H$_2$O; MW 434.5 | | | | | | |
|---|---|---|---|---|---|---|
| calculated | C | 44.22 | H | 4.64 | N | 16.12 |
| found | | 44.02 | | 4.57 | | 16.07 |

EXAMPLE 20

Preparation of the compound of formula

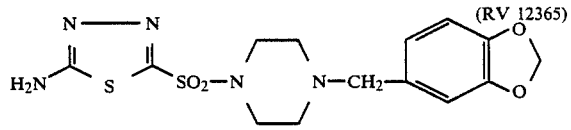
(RV 12365)

The compound obtained in Example 19 was hydrolysed in ethanol containing HCl in a weight ratio of 20:3 by heating to a temperature of between 50° and 80° C. for some hours.

The product obtained was isolated from the reaction mixture as described in the preceding examples, and recrystallised from ethanol. Yield 93%.

M.P.=205°–208° C.

| Percentage analysis: C$_{14}$H$_{17}$N$_5$O$_4$S$_2$.½H$_2$O; MW 392.45 | | | | | | |
|---|---|---|---|---|---|---|
| calculated | C | 42.84 | H | 4.62 | N | 17.84 |
| found | | 42.86 | | 4.54 | | 17.67 |

EXAMPLE 21

Preparation of the compound of formula

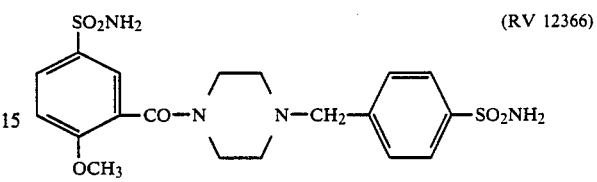
(RV 12366)

The N(2-methoxy-5-sulphamoyl)benzoyl-piperazine obtained as described in Example 9 was reacted with 4-sulphamido-benzyl chloride in a 1.1 N aqueous NaOH solution.

The mixture was kept under agitation for 3 hours at a temperature of 80°–100° C.

On cooling the aqueous solution, the desired compound precipitated and was purified by crystallisation from methanol. Yield 69%.

M.P.=182°–184° C.

| Percentage analysis: C$_{19}$H$_{24}$N$_4$O$_6$S$_2$; MW 468.55 | | | | | | |
|---|---|---|---|---|---|---|
| calculated | C | 48.70 | H | 5.15 | N | 11.95 |
| found | | 48.56 | | 5.18 | | 11.79 |

EXAMPLE 22

Preparation of the compound of formula

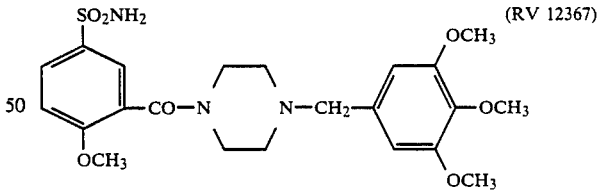
(RV 12367)

The N-(2-methoxy-5-sulphamoyl)benzoyl-piperazine obtained as described in Example 9 was reacted under reflux for some hours with 3,4,5-trimethoxy-benzyl-chloride in stoichiometric ratio in a 1:1 chloroform: ethanol mixture in the presence of pyridine.

The reaction mixture was evaporated under vacuum, taken up in dilute sodium hydroxide solution, washed with chloroform, acidified with acetic acid and filtered over carbon.

The clear solution was alkalised with concentrated KOH under agitation. The precipitate was filtered off, washed with water and purified with silica gel. Yield 45%.

M.P.=176°–178° C. (hydrochloride)

| Percentage analysis: C22H29N3O7S; MW 479.53 | | | | | | |
|---|---|---|---|---|---|---|
| calculated | C | 55.10 | H | 6.09 | N | 8.76 |
| found | | 55.21 | | 6.12 | | 8.61 |

EXAMPLE 23

Preparation of the compound of formula

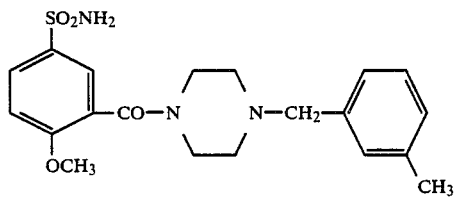

(RV 12368)

The N(2-methoxy-5-sulphamoyl)benzoyl-piperazine obtained as described in Example 9 was reacted with 3-methyl-benzylchloride in stoichiometric ratio in an aqueous dilute NaOH solution.

The mixture was heated to a temperature of 50° C. for 2 hours.

The desired product precipitated on cooling, and was recrystallised from isopropyl alcohol. Yield 50%.

M.P.=180°–181° C.

| Percentage analysis: C20H25N3O4S; MW 403.50 | | | | | | |
|---|---|---|---|---|---|---|
| calculated | C | 59.53 | H | 6.24 | N | 10.41 |
| found | | 59.30 | | 6.02 | | 10.20 |

EXAMPLE 24

Preparation of the compound of formula

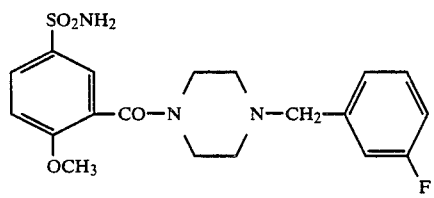

(RV 12369)

The N-(2-methoxy-5-sulphamoyl)benzoyl-piperazine obtained as described in Example 9 was reacted with 3F-benzylchloride in stoichiometric ratio in an aqueous alkaline solution at a temperature of 80°–100° C. for 2 hours, The desired product precipitated on cooling, and was recrystallised from isopropyl alcohol. Yield 35%.

M.P.=175°–176° C.

| Percentage analysis: C19H22N3O4S; MW 407.46 | | | | | | |
|---|---|---|---|---|---|---|
| calculated | C | 56.00 | H | 5.44 | N | 10.31 |
| found | | 55.83 | | 5.41 | | 10.55 |

EXAMPLE 25

Preparation of the compound of formula

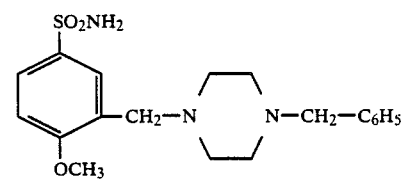

(RV 12359)

Benzyl-piperazine and 2-methoxy-5-sulphamoyl-methylenechloride in stoichiometric ratio were fed in chloroform solution into a reactor.

The mixture was kept under reflux for 4 hours.

When the reaction terminated, the mixture was poured into ice and acidified with HCl.

The precipitated hydrochloride was purified by crystallisation from ethanol. It was dissolved in water and precipitated with ammonia. It was filtered off, washed with water and crystallised from ethanol. Yield 47%.

M.P.=160°–164° C.

| Percentage analysis: C19H25N3O3S; MW 375.48 | | | | | | |
|---|---|---|---|---|---|---|
| calculated | C | 60.77 | H | 6.71 | N | 11.19 |
| found | | 60.60 | | 6.65 | | 11.04 |

We claim:

1. A piperazino compound of the formula

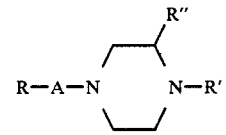

in which:

A is CO, CH2 or SO2;

R is 2-methoxy-5-sulphamoyl-phenyl, 2-sulphamoylimidazyl, 2-amino-1,3,4-thiadiazole or 2-acetamido-1,3,4-thiadiazole;

R' is H, linear or branched C1–C6 alkyl; linear or branched C2–C6 alkenyl; alkyl-phenyl or alkenyl-phenyl, wherein phenyl is optionally monosubstituted with halogen, trihalomethyl, C1–C6 alkyl, C1–C6 alkoxy, or sulphonamido; C2–C6 aliphatic acyl; C3–C6 alkylcarboxyalkoxy; alkyl-carboxyamino in which the alkyl is C1–C3 and the amine is mono or disubstituted by linear or branched C1–C6 alkyl and;

R" is H, or together with R' forms a 5 or 6 membered ring condensed with the piperazine;

provided that when R is a substituted phenyl group and A is CO, R' is other than H, C1–C4 alkyl or benzyl.

* * * * *